United States Patent
Laine et al.

(10) Patent No.: US 10,296,709 B2
(45) Date of Patent: May 21, 2019

(54) PRIVACY-PRESERVING GENOMIC PREDICTION

(71) Applicant: Microsoft Technology Licensing, LLC, Redmond, WA (US)

(72) Inventors: Kim Laine, Seattle, WA (US); Nicolo Fusi, Boston, MA (US); Ran Gilad-Bachrach, Bellevue, WA (US); Kristin E. Lauter, La Jolla, CA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 339 days.

(21) Appl. No.: 15/179,777

(22) Filed: Jun. 10, 2016

(65) Prior Publication Data
US 2017/0357749 A1 Dec. 14, 2017

(51) Int. Cl.
*G06F 17/50* (2006.01)
*G06F 19/12* (2011.01)
(Continued)

(52) U.S. Cl.
CPC .............. *G06F 19/12* (2013.01); *G06F 19/18* (2013.01); *G06F 19/24* (2013.01);
(Continued)

(58) Field of Classification Search
CPC ............................... G06F 17/5018; H04L 9/08
(Continued)

(56) References Cited

U.S. PATENT DOCUMENTS 7,620,625 B2 11/2009 Ramzan et al.
8,515,058 B1 8/2013 Gentry
(Continued)

FOREIGN PATENT DOCUMENTS

CN 101057448 A 10/2007
CN 103425933 A 12/2013
(Continued)

OTHER PUBLICATIONS

Brakerski, et al., "(Leveled) Fully Homomorphic Encryption without Bootstrapping", ACM Transactions on Computation Theory, vol. 6, No. 3, Article 13, Jul. 2014, 36 pgs.
(Continued)

*Primary Examiner* — Andy Ho
(74) *Attorney, Agent, or Firm* — Merchant & Gould (57) ABSTRACT

The techniques and/or systems described herein are directed to improvements in genomic prediction using homomorphic encryption. For example, a genomic model can be generated by a prediction service provider to predict a risk of a disease or a presence of genetic traits. Genomic data corresponding to a genetic profile of an individual can be batch encoded into a plurality of polynomials, homomorphically encrypted, and provided to a service provider for evaluation. The genomic model can be batch encoded as well, and the genetic prediction may be determined by evaluating a dot product of the genomic model data the genomic data. A genomic prediction result value can be provided to a computing device associated with a user for subsequent decrypting and decoding. Homomorphic encoding and encryption can be used such that the genomic data may be applied to the prediction model and a result can be obtained without revealing any information about the model, the genomic data, or any genomic prediction.

20 Claims, 5 Drawing Sheets

(51) Int. Cl.
G06F 19/18 (2011.01)
G06F 19/24 (2011.01)
G06F 21/62 (2013.01)
H04L 9/00 (2006.01)

(52) U.S. Cl.
CPC ...... *G06F 21/6245* (2013.01); *G06F 21/6254* (2013.01); *H04L 9/008* (2013.01)

(58) Field of Classification Search
USPC .............................................. 703/2; 380/277
See application file for complete search history.

(56) References Cited

U.S. PATENT DOCUMENTS

| | | | |
|---|---|---|---|
| 8,565,435 | B2 | 10/2013 | Gentry et al. |
| 8,861,716 | B2 | 10/2014 | Halevi et al. |
| 8,925,075 | B2 | 12/2014 | Krendelev et al. |
| 8,958,555 | B2 | 2/2015 | Gentry et al. |
| 8,972,742 | B2 | 3/2015 | Troncoso Pastoriza et al. |
| 9,083,526 | B2 | 7/2015 | Gentry |
| 9,306,738 | B2 | 4/2016 | Loftus et al. |
| 9,524,370 | B2* | 12/2016 | Raisaro .................. H04L 9/008 |
| 9,536,047 | B2* | 1/2017 | Ayday .................. G06F 19/322 |
| 9,819,650 | B2* | 11/2017 | Soon-Shiong ...... H04L 63/0428 |
| 9,935,765 | B2* | 4/2018 | Weaver .................. G16H 50/30 |
| 2004/0078407 | A1 | 4/2004 | Naslund et al. |
| 2004/0086113 | A1 | 5/2004 | Lauter et al. |
| 2004/0143403 | A1 | 7/2004 | Brandon et al. |
| 2011/0110525 | A1 | 5/2011 | Gentry |
| 2012/0039463 | A1 | 2/2012 | Gentry et al. |
| 2012/0201378 | A1 | 8/2012 | Nabeel et al. |
| 2013/0097417 | A1 | 4/2013 | Lauter et al. |
| 2013/0150253 | A1 | 6/2013 | Deciu et al. |
| 2013/0170640 | A1 | 7/2013 | Gentry |
| 2013/0216044 | A1 | 8/2013 | Gentry et al. |
| 2013/0329883 | A1 | 12/2013 | Tamayo-rios |
| 2013/0339722 | A1 | 12/2013 | Krendelev et al. |
| 2014/0177828 | A1 | 6/2014 | Loftus et al. |
| 2014/0372769 | A1 | 12/2014 | Kerschbaum et al. |
| 2015/0039912 | A1 | 2/2015 | Payton et al. |
| 2015/0154406 | A1 | 6/2015 | Naehrig et al. |
| 2015/0213079 | A1 | 7/2015 | Shukla et al. |
| 2016/0110500 | A1 | 4/2016 | Wang et al. |
| 2016/0119119 | A1 | 4/2016 | Calapodescu et al. |
| 2016/0182226 | A1 | 6/2016 | Yasuda et al. |
| 2016/0191233 | A1 | 6/2016 | Loftus et al. |
| 2016/0352510 | A1 | 12/2016 | Morikawa et al. |
| 2016/0352710 | A1 | 12/2016 | Hibshoosh et al. |
| 2017/0134156 | A1 | 5/2017 | Laine et al. |
| 2017/0180115 | A1 | 6/2017 | Laine et al. |
| 2017/0242961 | A1* | 8/2017 | Shukla .................. G06F 21/32 |

FOREIGN PATENT DOCUMENTS

| | | |
|---|---|---|
| WO | 2012149395 A1 | 11/2012 |
| WO | WO2012158621 A1 | 11/2012 |
| WO | 2013067542 A1 | 5/2013 |
| WO | 2015112859 A1 | 7/2015 |

OTHER PUBLICATIONS

Halevi et al., "Design and Implementation of a Homomorphic Encryption Library", Nov. 30, 2012, retrieved from http://researcher.ibm.com/researcher/files/us-shaih/he-library.pdf, 42 pgs.

International Search Report and Written Opinion received for PCT Patent Application No. PCT/US2016/060027, dated Feb. 22, 2017, 12 pages.

International Search Report and Written Opinion received for PCT Patent Application No. PCT/US2016/060038, dated Feb. 23, 2017, 12 pages.

Office action for U.S. Appl. No. 14/934,039, dated Feb. 27, 2017, Laine et al., "Homomorphic Encryption with Optimized Parameter Selection",17 pages.

Okamoto, et al, "Homomorphic Encryption and Signatures from Vector Decomposition", 2008, Retrived from the Internet, <<http://link.springer.com/chapter/10.1007/978-3-540-85538-5_4>>, Intl Conf on Pairing Based Cryptography Sep. 2008, pp. 58-74.

Ayday, et al., "Privacy-Preserving Computation of Disease Risk by Using Genomic, Clinical, and Environmental Data", In Proceedings of the USENIX confernece on Safety, Security, Privacy and Interoperability of Health Information Technologies, Aug. 12, 2013, 10 pages.

Wang, et al., "HEALER: Homomorphic computation of exact logistic regression for secure rare disease variants analysis in GWAS", In Journal of Bioinformatics, vol. 32, Issue 2, Oct. 6, 2015, 8 pages.

Ayday, et al., "Personal use of the genomic data: Privacy vs. storage cost", In Proceedings of IEEE Global Communications Conference, Dec. 9, 2013, pp. 2723-2729.

Wang, et al., "Efficient Genome-Wide, Privacy-Preserving Similar Patient Query based on Private Edit Distance", In Proceedings of the 22nd ACM SIGSAC Conference on Computer and Communications Security, Oct. 12, 2015, 12 pages.

Zhang, et al., "FORESEE: Fully Outsourced secuRe gEnome Study basEd on homomorphic Encryption", In Journal of BMC Medical Informatics and Decision Making, vol. 15, Dec. 21, 2015, pp. 1-14.

Torres, et al al., "Effectiveness of Fully Homomorphic Encryption to Preserve the Privacy of Biometric Data", In Proceedings of the 16th International Conference on Information Integration and Web-based Applications & Services, Dec. 4, 2014, 7 pages.

Bos, et al., "Improved Security for a Ring-Based Fully Homomorphic Encryption Scheme", In Proceedings of 14th IMA International Conference on Cryptography and Coding, Dec. 17, 2013, 30 pages.

Bos, et al., "Private Predictive Analysis on Encrypted Medical Data", In Journal of Biomedical Informatics, vol. 50, Aug. 2014, pp. 234-243.

Bosma et al., "The Magma Algebra System I: The User Language", In Journal of Symbolic Computation, vol. 24, Issue 3-4, Sep. 1997, pp. 235-265.

Brakerski, Zvika, "Fully Homomorphic Encryption without Modulus Switching from Classical GapSVP", In Proceedings of 32nd Annual Cryptology Conference, Aug. 19, 2012, pp. 868-886.

Brakerski, et al., "Packed Ciphertexts in LWE-Based Homomorphic Encryption", In Proceedings of 16th International Conference on Practice and Theory in Public-Key Cryptography, Sep. 2012, pp. 1-12.

Brakerski, et al., "(Leveled) Fully Homomorphic Encryption without Bootstrapping", In Proceedings of 3rd Innovations in Theoretical Computer Science Conference, Jan. 8, 2012, pp. 309-325.

Brakerski, et al., "Classical Hardness of Learning with Errors", In Proceedings of Forty-Fifth Annual ACM Symposium on Theory of Computing, Jun. 1, 2013, pp. 575-584.

Brakerski, et al., "Efficient Fully Homomorphic Encryption from (Standard) LWE", In Proceedings of IEEE 52nd 4nnual Symposium on Foundations of Computer Science, Oct. 22, 2011, pp. 97-106.

Brakerski, et al., "Fully Homomorphic Encryption from Ring-LWE and Security for Key Dependent Messages", In Proceedings of 31st Annual Cryptology Conference, Aug. 14, 2011, pp. 505-524.

Brakerski, et al., "Lattice-based FHE as Secure as PKE", In Proceedings of 5th Conference on Innovations in Theoretical Computer Science, Jan. 12, 2014, pp. 1-12.

Cheon, et al., "Homomorphic Computation of Edit Distance", In Proceedings of 3rd Workshop on Encrypted Computing and Applied Homomorphic Cryptography, Jan. 30, 2015, pp. 1-16.

Fan, et al., "Somewhat Practical Fully Homomorphic Encryption", In Journal of IACR Cryptology, Retrieved on: May 19, 2015, pp. 1-19.

Festa, et al., "Nuclear Magnetic Resonance Lipoprotein Abnormalities in Prediabetic Subjects in the Insulin Resistance Atherosclerosis Study", In Journal of Circulation, vol. 111, Issue 25, Jun. 28, 2005, pp. 3465-3472.

Gentry, Craig, "Fully Homomorphic Encryption Using Ideal Lattices", In Proceedings of Forty-First Annual ACM Symposium on Theory of Computing, May 31, 2009, pp. 169-178.

(56) References Cited

OTHER PUBLICATIONS

Gentry, et al., "Homomorphic Evaluation of the Aes Circuit", In Proceedings of 32nd Annual Cryptology Conference, Jan. 2015, 35 pages.
Gentry, et al., "Homomorphic Encryption from Learning with Errors: Conceptually-Simpler, Asymptotically-Faster, Attribute-Based", In Proceedings of 33rd Annual Cryptology Conference on Advances in Cryptology, vol. 8042, Jun. 2013, pp. 1-25.
Lepoint, et al., "A Comparison of the Homomorphic Encryption Schemes FV and YASHE", In Proceedings of 7th International Conference on Cryptology in Africa, May 28, 2014, pp. 1-18.
Lindner, et al., "Better Key Sizes (and Attacks) for LWE-Based Encryption", In Proceedings of the 11th international conference on Topics in cryptology, Nov. 2010, pp. 1-21.
Micciancio, et al., "Trapdoors for Lattices: Simpler, Tighter, Faster, Smaller", In Proceedings of 31st Annual International Conference on the Theory and Applications of Cryptographic Techniques, Apr. 15, 2012, 18 pages.
Lauter, et al., "Can homomorphic encryption be practical?", In Proceedings of the 3rd ACM workshop on Cloud computing security workshop, Oct. 21, 2011, pp. 113-124.
Lyubashevsky, et al., "On Ideal Lattices and Learning with Errors over Rings", In Journal of the ACM, vol. 60, Issue 6, Nov. 2013, 35 pages.
Peikert, Chris, "Public-key cryptosystems from the worst-case shortest vector problem", In Proceedings of the forty-first annual ACM symposium on Theory of computing, May 31, 2009, pp. 333-342.
"R: A Language and Environment for Statistical Computing", In Publication of R Foundation for Statistical Computing, Nov. 30, 2009, 3503 pages.
Regev, Oded, "On lattices, learning with errors, random linear codes, and cryptography", In Journal of the ACM vol. 56, Issue 6, Sep. 2009, 40 pages.
Smart, et al., "Fully homomorphic SIMD operations", In Journal of Designs, Codes and Cryptography, vol. 71, Issue 1, Apr. 1, 2014, 19 pages.
Stehlé, et al., "Making NTRU as secure as worst-case problems over ideal lattices", In Proceedings of the 30th Annual international conference on Theory and applications of cryptographic techniques: advances in cryptology, May 15, 2011, 20 pages.
Tabaei, et al., "A multivariate logistic regression equation to screen for diabetes development and validation", In Journal of Diabetes Care, vol. 25, No. 11, Nov. 2002, pp. 1999-2003.
Pol, et al., "Estimating key sizes for high dimensional lattice-based systems", In Proceedings of 14th IMA International Conference on Cryptography and Coding, Dec. 17, 2013, pp. 1-11.
Dijk, et al., "Fully homomorphic encryption over the integers", In Proceedings of 29th Annual International Conference on the Theory and Applications of Cryptographic Techniques, May 30, 2010, 21 pages.
Dowlin, et al., "Manual for Using Homomorphic Encryption for Bioinformatics", In TechReport MSR-TR-2015-87, Nov. 13, 2015, pp. 1-16.
Eisenbud, David., "Commutative Algebra: with a view toward algebraic geometry", Book, Chapt 2, 2.6 Exercises, pp. 79-86, Mar. 30, 1995.
López-Alt, et al., "On-the-fly multiparty computation on the cloud via multikey fully homomorphic encryption", In Proceedings of the forty-fourth annual ACM symposium on Theory of computing, May 19, 2012, pp. 1219-1234.
McLaren, et al., "Privacy-preserving genomic testing in the clinic: a model using HIV treatment", In Journal of Genetics in Medicine, Jan. 14, 2016, pp. 1-9.
Lauter, et al., "Private Computation on Encrypted Genomic Data", In TechReport MSR-TR-2014-93, Jun. 2014, pp. 1-21.
Kim, et al., "Private Genome Analysis through Homomorphic Encryption", In Journal of BMC medical informatics and decision making, vol. 15, Dec. 2015, pp. 1-18.

U.S. Appl. No. 14/934,039, Lauter, et al., "FHELib: Homomorphic Encryption with Optimized Encodings and Parameter Selection", filed Nov. 5, 2015.
U.S. Appl. No. 14/934,048, Lauter, et al., "FHELib: Homomorphic Encryption with Optimized Encodings and Parameter Selection", filed Nov. 5, 2015.
Ayday et al, "Privacy Enhancing Technologies for Medical Tests Using Genomic Data", 20th Network and Distribution System Security Symposium, Feb. 2013, 3 pgs.
Basilakis, et al., "The Potential for Machine Learning Analysis over Encrypted Data in Cloud-based Clinical Decision Support—Background and Review", Proceedings of the 8th Australasian Workshop on Health Informatics and Knowledge Management, Jan. 27, 2015, pp. 3-13.
Bergh, Petter Andreas, "Ext-symmetry over quantum complete intersections", Archives of Mathematics, May 2009, 6 pages.
Betley, et al., "The cyclotomic trace and curves on K-theory", Topology, Pergamon, Jul. 2005, 30 pages.
Boneh et al, "Private Database Queries Using Somewhat Homomorphic Encryption", Applied Cryptography and Network Security, Jun. 2013, 21 pgs.
Bos et al., "Leveled Homomorphic Encryption with Smaller Ciphertexts", unknown publication date, 18 pages.
Boyar et al., "A depth-16 circuit for the AES S-box", National Institute of Standards and Technology, Dec. 2011, 11 pages.
Brakerski et al., "Fully Homomorphic Encryption from Ring-LWE and Security for Key Dependent Messages", Proceedings of the 31st annual conference on Advances in cryptology, Aug. 2011, 20 pages.
Brakerski et al., "Fully Homomorphic Encryption without Bootstrapping", Association for Computing Machinery, Jan. 2008, 27 pages.
Cetin et al, "An Investigation of Complex Operations with Word-Size Homomorphic Encryption", Dec. 2015, Cryptology ePrint Archive, Report 2015/1195, 16 pgs.
Clarke et al, "Basic Statistical Anaylsis in Genetic Case Control Studies", Nat Protoc, vol. 6, Feb. 2011, 28 pgs.
Domingo-Ferrer, et al., "Privacy Homomorphisms for Social Networks With Private Relationships", In Proceedings of the International Journal of Computer and Telecommunications Networking, Jul. 28, 2008, pp. 1-10.
Doroz, et al., "Accelerating Fully Homomorphic Encryption in Hardware", Published on: Sep. 2013, Available at http://ecewp.ece.wpi.edu/wordpress/vernam/files/2013/09/Accelerating-Fully-Homomorphic-Encryption-in-Hardware.pdf, 14 pgs.
Duan et al., "Practical Private Computation and Zero-Knowledge Tools for Privacy-Preserving Distributed Data Mining", Proc 2008 SIAM Intl Conf on Data Mining, Apr. 2008, 12 pages.
Furihata et al, "Test of Association Between Haplotypes andPhenotypes in Case Control Studies: Examination of Validity of the Application of an Algorithm for Samples from Cohort or Clinicial trials to Case Control Samples Using Simulated and Real Data", Genetics, vol. 174, Issue 3, Nov. 2006, 12 pgs.
Gentry, "A Fully Homomorphic Encryption Scheme", Sep. 2009 Dissertation, 209 pgs.
Gentry et al., "Homomorphic Evaluation of the AES Circuit", International Association for Cryptologic Research, Jun. 15, 2012, 34 pages.
Gentry et al., "Better Bootstrapping in Fully Homomorphic Encryption", Public Key Cryptography, Dec. 15, 2011, 22 pages.
Gentry et ai.,"Fully Homomorphic Encryption with Polylog Overhead", International Association for Cryptologic Research, Oct. 2011, 40 pages.
Graepel et al., "ML Confidential: Machine Learning on Encrypted Data", Proc 15th intl conf on Information Security and Cryptology, Sep. 2012, 10 pages.
Hu, et al., "Improving the Efficiency of Homomorphic Encryption Schemes", In Thesis of Electrical and Computer Engineering, May 2013, 103 pages.
International Search Report and Written Opinion received for PCT Patent Application No. PCT/U52013/077348, dated Jun. 30, 2014, 18 pages.
PCT Intl Search Report and Written Opinion for PCT/US2014/066992, dated Mar. 10, 2015, 12 pages.

(56) References Cited

OTHER PUBLICATIONS

Oracle, "Platform-as-a-Service Private Cloud with Oracle Fusion Middleware", An Oracle White Paper, Oct. 2009, 20 pages (Author unknown).
Qin et al., "An FPGA Design of AES Encryption Circuit with 128-bit Keys", GLSVLSI'05, Apr. 2005, 5 pages.
Ramaekers, Coen, "Fully Homomorphic Encryption in JCrypTool", Aug. 4, 2011, 85 pages.
Stehle et al., "Faster Fully Homomorphic Encryption", Chapt, Advances in Cryptology, ASIACRYPT 2010, vol. 6477 of series Lecture Notes in Computer Science, Sep. 2010, 25 pgs.
Wang, et al., "Accelerating Fully Homomorphic Encryption Using GPU", In Proceedings of IEEE Conference on High Performance Extreme Computing, Sep. 10, 2012, 5 pages.
Wang, et al., "Exploring the Feasibility of Fully Homomorphic Encryption", Published on: Dec. 2012, Available at: http://ecewp.ece.wpi.edu/wordpress/crypto/files/2012/12/journal0705.pdf, 8 pgs.
Xie, et al., "Crypto-Nets: Neural Networks Over Encrypted Data", In Proceedings of 3rd International Conference on Learning Representations, May 7, 2015, pp. 1-9.
Yasuda et al, "Secure Pattern Matching using Somewhat Homomorphic Encryption", Proc ACM Workshop on Cloud Computing Security, Nov. 2013, 12 pgs.
"Non-Final Office Action Issued in U.S. Appl. No. 13/723,879", dated Jun. 17, 2015, 9 Pages.
"Non Final Office Action Issued in U.S. Appl. No. 14/093,427", dated May 6, 2016, 14 Pages.
"Final Office Action Issued in U.S. Appl. No. 14/934,039", dated Jun. 15, 2017, 21 Pages.
"Notice of Allowance Issued in U.S. Appl. No. 14/934,039", dated May 9, 2018, 9 Pages.
"Final Office Action Issued in U.S. Appl. No. 14/934,048", dated Dec. 5, 2017, 19 Pages.
"Non Final Office Action Issued in U.S. Appl. No. 14/934,048", dated Jul. 28, 2017, 19 Pages.
"Non Final Office Action Issued in U.S. Appl. No. 14/975,528", dated Jul. 7, 2017, 12 Pages.
"Final Office Action Issued in U.S. Appl. No. 15/062,597", dated May 19, 2017, 11 Pages.
"Final Office Action Issued in U.S. Appl. No. 15/062,597", dated May 15, 2018, 11 Pages.
"Non Final Office Action Issued in U.S. Appl. No. 15/062,597", dated Oct. 18, 2017, 11 Pages.
"Non Final Office Action Issued in U.S. Appl. No. 15/062,597", dated Nov. 4, 2016, 11 Pages.
"First Office Action and Search Report Issued in Chinese Patent Application No. 201380067538.8", dated Aug. 3, 2017, 15 Pages.
"Second Office Action Issued in Chinese Patent Application No. 201380067538.8", dated Apr. 11, 2018, 6 Pages.
"International Preliminary Report on Patentability Issued in PCT Application No. PCT/US2013/077348", dated Dec. 3, 2014, 7 Pages.
"International Preliminary Report on Patentability Issued in PCT Application No. PCT/US2014/066992", dated Jun. 9, 2016, 11 Pages.
"International Preliminary Report on Patentability Issued in PCT Application No. PCT/US2016/060027", dated May 17, 2018, 9 Pages.
"International Preliminary Report on Patentability issued in PCT Application No. PCT/US2016/060038", dated Feb. 14, 2018, 11 Pages.
"Second Written Opinion Issued in PCT Application No. PCT/US2016/060038", dated Sep. 28, 2017, 9 Pages.

* cited by examiner

DETERMINE $n$, WHERE $n$ IS THE MAXIMUM NUMBER OF TERMS IN THE PLAINTEXT AND CIPHERTEXT POLYNOMIALS 402 → 404 → $n = 1024, 2048, 4096, 8192, 16384$

DETERMINE $t \equiv 1 \pmod{2n}$, WHERE $t$ IS PRIME 406 → 408 → $t = 137674753$ (28 bits)

DETERMINE $q$ IN THE FORM OF $q = 2^A - B + 1$, WHERE $q \equiv 1 \pmod t$ 410 → 412 → $q = 2^{96} - 1757273$ DETERMINE $x_{key}$ AS A PROBABILITY DISTRIBUTION ON POLYNOMIALS OF DEGREE AT MOST $n-1$ FOR KEY GENERATION 414 → 416 → $x_{key}$ = uniform distribution on $\{-1, 0, 1\}$ DETERMINE $x_{err}$ AS A PROBABILITY DISTRIBUTION ON POLYNOMIALS AT MOST $n-1$ FOR KEY GENERATION AND ENCRYPTION 418 → 420 → $x_{err}$ = truncated discrete Gaussian distribution centered at zero, $\sigma = 3.19$ TRANSMIT PARAMETERS $(n, q, t, x_{key}, x_{err})$ 422 → 424 →

500 ⟶

RECEIVING GENOMIC DATA ASSOCIATED WITH AN INDIVIDUAL, THE GENOMIC DATA INCLUDING A FIRST REPRESENTATION OF A PLURALITY OF GENETIC MUTATIONS BATCH ENCODED AS A FIRST PLURALITY OF POLYNOMIALS AND ENCRYPTED IN ACCORDANCE WITH A HOMOMORPHIC ENCRYPTION SCHEME
502

↓

RECEIVING GENOMIC MODEL DATA, THE GENOMIC MODEL DATA INCLUDING A SECOND REPRESENTATION OF A PLURALITY OF COEFFICIENTS DETERMINED USING MACHINE LEARNING, THE GENOMIC MODEL DATA BATCH ENCODED AS A SECOND PLURALITY OF POLYNOMIALS
504

↓

COMPUTING, AS A GENOMIC RESULT VALUE, A DOT PRODUCT OF THE GENOMIC DATA AND THE GENOMIC MODEL DATA, THE DOT PRODUCT BASED AT LEAST IN PART ON A SUM OF PRODUCTS OF CORRESPONDING ELEMENTS IN THE FIRST REPRESENTATION AND THE SECOND REPRESENTATION
506

↓

TRANSMITTING THE GENOMIC RESULT VALUE TO A COMPUTING DEVICE ASSOCIATED WITH THE INDIVIDUAL, THE GENOMIC RESULT VALUE INCLUDING AT LEAST ONE GENOMIC PREDICTION ASSOCIATED WITH THE GENOMIC DATA
508

FIG. 5

PRIVACY-PRESERVING GENOMIC PREDICTION

BACKGROUND

The development of cloud storage and services has allowed users to offload and/or outsource both storage of their data and associated computations on that data. As a result, businesses can choose to forego the expensive proposition of maintaining their own data centers, relying instead on cloud storage and computational services. In addition to storing data in remote servers, computations can be performed in remote servers as well.

One type of data amenable to cloud storage and computational services is genomic data. The field of genomics involves analyzing the function and structure of genomes, including DNA sequencing and genetic mapping. Human genomic data can be mined to identify variants in genes that can contribute to diseases. However, a large and diverse genomic data set is needed to identify these genetic links. To this end, large databases of genomic data, as well as other types of data, are being established.

Maintaining data confidentiality is an especially important concern for storing data and performing computations on data in remote servers. Encryption schemes represent one form of technology directed towards securing data when stored in memory, when operated on, and/or transmitted over networks.

SUMMARY

The techniques and/or systems described herein are directed to improvements in genomic prediction using homomorphic encryption to evaluate genomic predictions from linear models on thousands or millions of genetic variants with improved processing and memory characteristics. For example, entities offering genomic prediction as a service may provide a prediction model in a form of a linear mixed model. Genomic data from an individual (e.g., a patient) may be provided in an encoded and encrypted form such that the genomic data may be applied to the prediction model and a result can be obtained without revealing any information about the model, the genomic data, or any genomic prediction. Genomic data can be encoded using batching, and a result may be quickly obtained as a dot product between the data and parameters constituting the prediction model and the genomic data. Although aspects of this disclosure refer to genomic predictions and/or genomic data, the techniques and/or systems described herein can be applied to any type of data and/or any type of predictions.

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. Furthermore, the claimed subject matter is not limited to implementations that solve any or all disadvantages noted in any part of this disclosure.

BRIEF DESCRIPTION OF THE DRAWINGS

The detailed description is described with reference to the accompanying figures. In the figures, the left-most digit(s) of a reference number identifies the figure in which the reference number first appears. The use of the same reference number in different figures indicates similar or identical items.

DETAILED DESCRIPTION

One of the key tasks in genomics and health is to predict a trait (or disease risk) given a set of single nucleotide polymorphisms (SNPs) or variants. In some instances, genomic prediction service providers can apply machine learning models on proprietary clinical data to develop a prediction model, with the purpose of offering trait predictions from genetic data as a service. Patient genomic data can be applied to the prediction model to provide some genetic prediction, such as a predicted risk of having a disease. It can be understood that the confidentiality of both the prediction model and the patient genomic data are paramount. In a time when data breaches are ever more common, the safety of genetic data both in transit (over the network) and at rest (in the cloud computing facilities) is of concern. Thus, encryption techniques can be applied to maintain confidentiality of data in this scenario.

An encryption scheme is said to be homomorphic when it allows for operations to be performed on encrypted data without requiring access to the secret key. In the scenario discussed above, a service provider would apply the prediction model to homomorphically encrypted data, and obtain an encryption of the prediction model applied to the underlying plaintext data, which can then be sent back to the data owner, who can decrypt it with the secret key.

As discussed herein, homomorphic encryption is used to enable secure prediction of traits from genetic data. In this approach, a patient's genetic data and the answer generated by the cloud service are encrypted at all times and can only be decrypted by the patient (or institution) requesting the prediction. In some instances, the genomic model data can be encrypted as well, maintaining the proprietary nature of the prediction model. In some instances, the genomic model data may remain unencrypted to simplify operations.

In general, a prediction service provider can include genomic researchers that apply machine learning models to a database of genomic data to develop a prediction model for predicting a presence of a disease or phenotype. In some instances, the prediction can be directed to binary predictions (e.g., yes or no), while in some instances, the prediction can be directed to continuous predictions (e.g., body mass index (BMI), height, blood cholesterol, etc.). In some instances, the prediction model may be a linear mixed model that, when applied to genomic data of a patient, provides a prediction of the target trait or mutation.

Genomic data of a patient can include a data vector corresponding to genetic variants (e.g., genetic mutations) of an individual. In order to reduce an amount of memory required to represent the genomic data as homomorphically encrypted data, the genomic data can be encoded using batching, which stores a plurality of data values in a single polynomial. In some instances, the genomic data can be encrypted into a plurality of polynomials. In some instances, the prediction model can be applied to the genomic data by computing the dot product. For example, the dot product of a genomic data vector g (of length n) and the model vector m (of length n) can include:

$$g \cdot m = g_1 \times m_1 + g_2 \times m_2 + \ldots + g_n \times m_n \quad (1)$$

Thus, homomorphic addition and multiplication can be used to evaluate genomic models and genomic data to provide an encrypted result to a user.

The techniques and/or systems described herein can improve a functioning of a computing device by reducing an amount of processing and/or by reducing an amount of memory required for performing computations on encrypted data. For example, the encoding techniques discussed herein can reduce a size of encoded data by batching genomic data into fewer polynomials, which can greatly improve processing time and reduce an amount of memory required during computations. Further, the encoding techniques can improve processing by obviating a need to perform any "bootstrapping" operations, which otherwise would be a huge computational burden to reformulate data during computations to remove noise. The techniques and/or systems discussed herein can improve the functioning of a computer and/or a network by improving the security of the data transmitted, operated on, and stored in a network. For example, the techniques described herein can allow encrypted data to be transmitted, operated on, and a result can be obtained, all without requiring the data to be decrypted or decoded on a remote server, thereby ensuring a confidentiality of the data. Further, the techniques and/or systems described herein allow clients to outsource computations to a network computer when a client does not have all the data required to run an algorithm.

Relative to non-optimized homomorphic encrypting using bitwise encryption, the encoding techniques discussed herein can decrease the size of data that needs to be transmitted over a network, thereby reducing congestion in a network, and further reducing an amount of processing required by components of the network. The optimization techniques and/or systems discussed herein further generate parameters which improves the functioning of a computing device by providing optimized parameters to reduce processing time and memory requirements.

Various examples for implementing homomorphic encryption using optimized encoding and parameter selection are described herein with reference to FIGS. 1-5.

Figure 1:
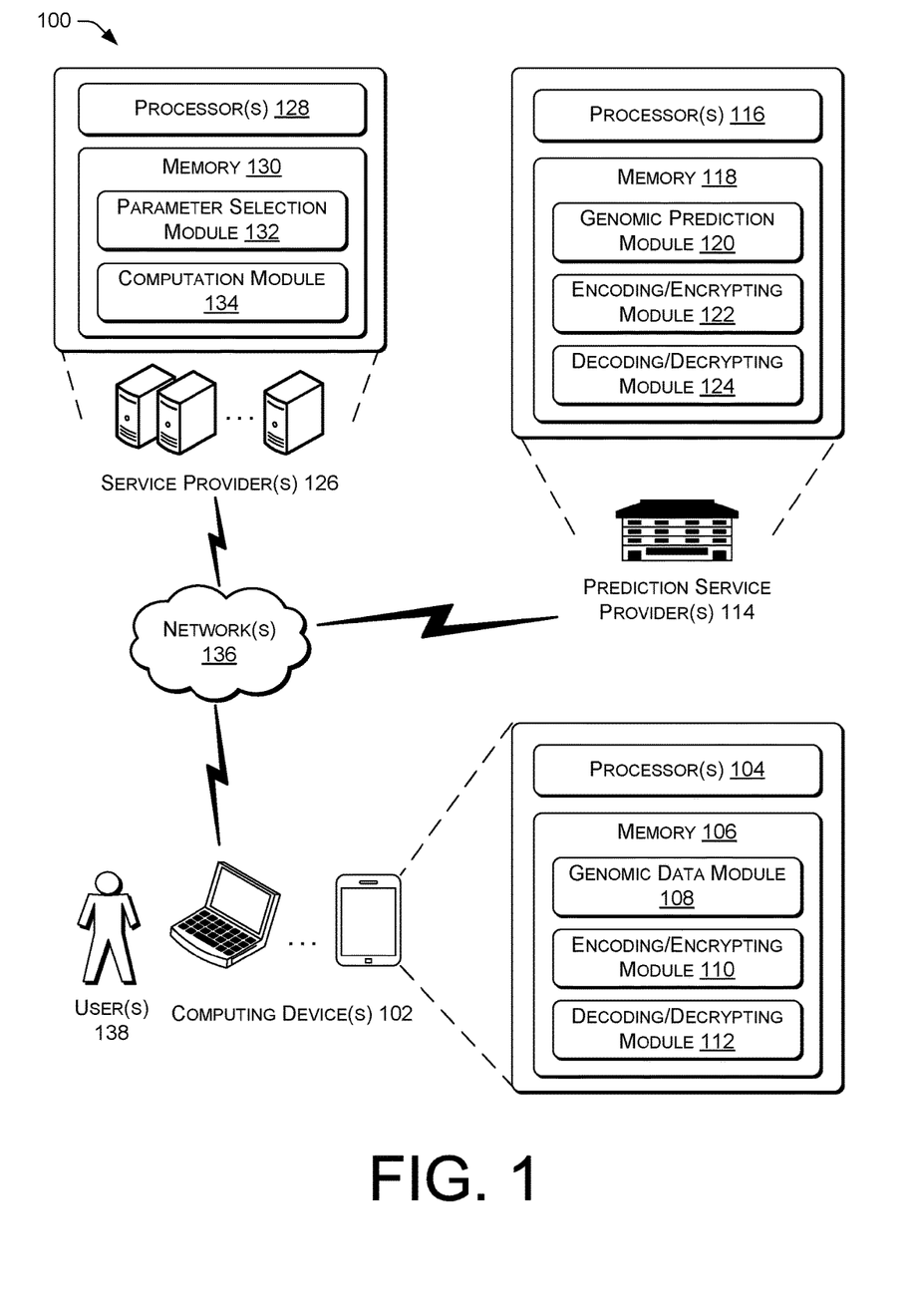
FIG. 1 illustrates an example environment for managing secure computations on encrypted data.

FIG. 1 illustrates an example environment 100 that is usable to implement the techniques and/or systems associated with the homomorphic encryption scheme described herein. The environment 100 includes computing device(s) 102 having processor(s) 104 and a memory 106 including a genomic data module 108, an encoding/encrypting module 110, and a decoding/decrypting module 112.

The environment 100 also includes prediction service provider(s) 114 having processor(s) 116 and a memory 118 including a genomic prediction module 120, an encoding/encrypting module 122, and a decoding/decrypting module 124.

The environment 100 also includes service provider(s) 126 to provide one or more services to the computing device 102 and/or the prediction service provider 114, such as the secure genomic prediction processing. To that end, the service provider 126 can include processor(s) 128 and a memory 130 including a parameter selection module 132 and a computation module 134 to provide the secure genomic prediction processing, which is explained in connection with the figures provided in this disclosure.

The computing device 102 can include, but is not limited to, any one of a variety of computing devices, such as a smart phone, a mobile phone, a personal digital assistant (PDA), an electronic book device, a laptop computer, a desktop computer, a tablet computer, a portable computer, a gaming device, a personal media player device, a server computer, a wearable device, or any other electronic device.

As introduced above, the computing device 102 can include one or more processor(s) 104 and memory 106. The processor 104 can be a single processing unit or a number of units, each of which could include multiple different processing units. The processor 104 can include one or more microprocessors, microcomputers, microcontrollers, digital signal processors, central processing units (CPUs), graphics processing units (GPUs), security processors (e.g., secure cryptoprocessors), and/or other processors. Alternatively, or in addition, some or all of the techniques described herein can be performed, at least in part, by one or more hardware logic components. For example, and without limitation, illustrative types of hardware logic components that can be used include Field-Programmable Gate Arrays (FPGAs), Application-Specific Integrated Circuits (ASICs), Application-Specific Standard Products (ASSPs), state machines, Complex Programmable Logic Devices (CPLDs), other logic circuitry, systems on chips (SoCs), and/or any other devices that perform operations based on software and/or hardware coded instructions. Among other capabilities, the processor 104 can be configured to fetch and/or execute computer-readable instructions stored in the memory 106.

The memory 106 can include one or a combination of computer-readable media. As used herein, "computer-readable media" includes computer storage media and communication media.

Computer storage media includes volatile and non-volatile, removable and non-removable media implemented in any method or technology for storage of information, such as computer-readable instructions, data structures, program modules, or other data. Computer storage media includes, but is not limited to, Phase Change Memory (PCM), Static Random-Access Memory (SRAM), Dynamic Random-Access Memory (DRAM), other types of Random-Access Memory (RAM), Read-Only Memory (ROM), Electrically Erasable Programmable ROM (EEPROM), flash memory or other memory technology, Compact Disc ROM (CD-ROM), Digital Versatile Discs (DVD) or other optical storage, magnetic cassettes, magnetic tape, magnetic disk storage or other magnetic storage devices, or any other medium that can be used to store information for access by a computing device.

In contrast, communication media includes computer-readable instructions, data structures, program modules, or other data in a modulated data signal, such as a carrier wave. As defined herein, computer storage media does not include communication media.

In various embodiments, the computing device 102 can communicate with the prediction service provider 114 and/or the service provider 126 via one or more wired or wireless networks 136, such as the Internet, a Mobile Telephone Network (MTN), or other various communication technologies.

In various embodiments, the memory 106 can include an operating system configured to manage hardware and services within and coupled to the computing device 102 for the benefit of other components and other devices.

The modules discussed herein, such as the genomic data module 108, the genomic prediction module 120, the encoding/encrypting modules 110 and 122, the decoding/decrypting modules 112 and 124, the parameter selection module 132 and the computation module 134, for example, can include hardware and/or software components. For example, the modules can be implemented by one or more modules stored in the memory 106, 118, and 130, respectively, and/or by one or more components of the processors 104, 116, and 128, respectively. As used herein, the term "module" is intended to represent example divisions of software and/or firmware for purposes of discussion, and is not intended to represent any type of requirement or required method, manner or organization. Accordingly, while various "modules" are discussed, their functionality and/or similar functionality could be arranged differently (e.g., combined into a fewer number of modules, broken into a larger number of modules, etc.). Further, while certain functions are described herein as being implemented as software modules configured for execution by a processor, in other embodiments, any or all of the functions can be implemented (e.g., performed) in whole or in part by hardware logic components, such as FPGAs, ASICs, ASSPs, state machines, CPLDs, other logic circuitry, SoCs, and so on.

The genomic data module 108 can store patient genomic data including genomic vector data for genomic prediction processing. In some instances, the genomic data module 108 can store sequenced DNA of one or more individuals. In some instances, a genomic data vector can include thousands, hundreds of thousands, or millions of values representing genetic traits or mutations, such as loci, alleles, genes, phenotypes, etc.

The encoding/encrypting module 110 can perform operations to encode and/or encrypt data in accordance with embodiments of the disclosure. For example, the encoding/encrypting module 110 can utilize parameters generated by the service provider 126 to encode data using the techniques disclosed herein. Further, the encoding/encrypting module 110 can generate a public key based at least in part on the parameters generated by the service provider 126 to encrypt the encoded data.

The decoding/decrypting module 112 can perform operations to decrypt and/or decode data in accordance with embodiments of the disclosure. For example, the decoding/decrypting module 112 can utilize parameters generated by the service provider 126 to generate a secret key for decrypting the encrypted data. Further, the decoding/decrypting module 112 can decode the decrypted data to obtain a plaintext result.

The prediction service provider 114 can include one or more computing devices, such as one or more desktop computers, laptop computers, servers, and the like. The one or more computing devices can be configured in a cluster, data center, cloud computing environment, or a combination thereof. In one example, the one or more computing devices provide cloud computing resources, including computational resources, storage resources, and the like, that operate remotely from the computing device 102.

The one or more computing devices of the prediction service provider 114 can include one or more processor(s) 116 and memory 118. The one or more processor(s) 116 can comprise a single processing unit or a number of units, each of which could include multiple different processing units. The one or more processor(s) 116 can include, for example, one or more microprocessors, microcomputers, microcontrollers, digital signal processors, CPUs, GPUs, security processors (e.g., secure cryptoprocessors), etc.

The genomic prediction module 120 can perform operations to generate one or more genomic prediction models for use in providing genomic predictions. The genomic prediction module 120 can store a genomic prediction vector including coefficients determined via machine learning on clinical data. The genomic prediction module 120 can provide the genomic model vector to the encoding/encrypting module 122 to encode and/or encrypt the genomic model vector to provide to the service provider 126. In some instances, the genomic model vector can remain unencrypted to simplify processing. In some instances, the encoding/encrypting module 122 can provide similar functionality as the encoding/encrypting module 110. In some instances, the decoding/decrypting module 124 can provide similar functionality as the decoding/decrypting module 112, with any public and/or secret keys generated by the prediction service provider 114 providing confidentiality to the genomic prediction vector.

The service provider 126 can include one or more computing devices, such as one or more desktop computers, laptop computers, servers, and the like. The one or more computing devices can be configured in a cluster, data center, cloud computing environment, or a combination thereof. In one example, the one or more computing devices provide cloud computing resources, including computational resources, storage resources, and the like, that operate remotely from the computing device 102. Further, in some implementations, the service provider 126 can include some or all of the aspects of the prediction service provider 114.

The one or more computing devices of the service provider 126 can include one or more processor(s) 128 and memory 130. The one or more processor(s) 128 can comprise a single processing unit or a number of units, each of which could include multiple different processing units. The one or more processor(s) 128 can include, for example, one or more microprocessors, microcomputers, microcontrollers, digital signal processors, CPUs, GPUs, security processors (e.g., secure cryptoprocessors), etc.

The memory 130 can include a parameter selection module 132 for automatically selecting parameters to be provided to the computing device 102 and/or the prediction service provide 114 to encode and encrypt genomic data and genomic model data, respectively. As described below in connection with FIG. 4, the parameter selection module 132 can operate a program to determine operating parameters such as the parameters (n, q, t, $x_{key}$, $x_{err}$).

As discussed herein, both plaintext and ciphertexts (e.g., encoded data and encrypted data) can be represented as polynomials. Accordingly, the parameter n can correspond to a maximum number of terms in the polynomials, which is to say, the polynomials can be defined to be of degree at most n−1. In some instances, the number n is a power of 2, for example, 1024, 2048, 4096, or 8192. Further, a polynomial ($X^n$+1) can be referred to as a polynomial modulus.

The parameter q can be referred to as a coefficient modulus. The coefficient modulus can be a prime integer modulus used to reduce the coefficients of ciphertext polynomials. In other words, ciphertexts can be polynomials of degree at most n−1 with coefficient in $Z_q$.

The parameter t can be referred to as the plaintext modulus. In some instances, the parameter t can be a prime number. The plaintext modulus can be an integer modulus that can be used to reduce the coefficients of plaintext polynomials. In other words, plaintexts can be polynomials of degree at most n−1 with coefficient in $Z_t$.

The distribution $x_{key}$ can be referred to as a probability distribution on polynomials of degree at most n−1 with integer coefficients, which can be used to sample polynomials with small coefficients that are used in the key generation procedure. In some instances, the $x_{key}$ can be a uniform distribution on $\{-1, 0, 1\}$.

Similarly, in some instances, the distribution $x_{err}$ on polynomials of degree at most n−1 can be used to sample noise polynomials, which can be used during both key generation and encryption. In some instances, the $x_{err}$ can be a truncated discrete Gaussian distribution centered at zero, with standard deviation σ=3.19.

After parameters are generated and/or selected by the parameter selection module 132, the parameters can be transmitted to the computing device 102 and/or the prediction service provider 114, to be used by the encoding/encrypting modules 110 and 122 and/or by the decoding/decrypting modules 112 and 124.

In one particular implementation, the encoding/encrypting modules 110 and 122 can perform a key generation operation. On input of the encryption parameters parms:=(n, q, t, $x_{key}$,$x_{err}$), the key generation operation samples polynomials f′, g←$x_{key}$ from the key distribution, and sets f:=$[1+tf']_q$. If f is not invertible modulo q, the key generation operation chooses a new f′. Otherwise, the key generation operation can compute the inverse $f^{-1}$ off in $R_q$ and outputs the key pair $$(pk,sk):=(h,f)\in R\times R \qquad (2)$$

Further, in one particular implementation, the encoding/encrypting modules 110 and 122 can perform an operation to encrypt a plaintext element m∈$R_t$ by sampling a small error polynomial s,e←$x_{err}$, and outputs the ciphertext $$c:=[\lfloor q/t \rfloor m+e+hs]_q \in R \qquad (3)$$

In one particular implementation, the decoding/decrypting modules 112 and 124, given the k-th power of the private decryption key in $R_q$, and a ciphertext c, the decryption operations can recover the underlying message m using $$m=[\lfloor t/q \rfloor \cdot [f^k c]_q]_t \in R \qquad (4)$$

The memory 130 can also include a computation module 134 to perform computations on encoded data and/or encrypted data received from the computing device 102 and/or the prediction service provider 114. For example, the computation module 134 can evaluate the genomic data received from the computing device 102 and the genomic prediction model received from the prediction service provider 114 to provide a genomic result. In some instances, the computation module 134 can be a program such as a prediction engine, a machine learning program, an image analysis program, a financial program, or any other program that performs calculations on encrypted data. As can be understood in the context of this disclosure, the computation module 134 can include any program, computation, or operation that can be performed on data. In various embodiments, the computation module 134 can perform computations on the received encoded and/or encrypted data and can generate an encoded and/or encrypted result, which can be transmitted to the computing device 102 and/or the prediction service provider 114 for decryption and/or decoding by the decoding/decrypting modules 112 and/or 124.

In one particular implementation, the computation module 134 can perform computations in accordance with a homomorphic encryption scheme. The homomorphic encryption scheme operates in the quotient ring R:=$\mathbb{Z}[X]/(X^n+1)$, the elements of which can be polynomials with integer coefficients of degree less than n, where n can be a power of 2. In some instances, an element α∈R can be written as $\alpha=\sum_{i=0}^{n-1} a_i X^i$, with $a_i \in \mathbb{Z}$. In some instances, all plaintexts, ciphertexts, encryption and decryption keys, etc. are elements of the ring R, and have this form. In some instances, the addition operation in R can be done coefficient-wise, and a multiplication operation can be polynomial multiplication modulo $X^n+1$, e.g., polynomial multiplication followed by reduction modulo $X^n+1$. The reduction modulo $X^n+1$ can be carried out by replacing occurrences of $X^n$ with −1.

Further, the scheme can use the two integer moduli q and t, discussed above, for which q can be much larger than t. The coefficients of ciphertext and key elements are taken modulo q, whereas the coefficients of the plaintext elements are taken modulo t. In some instances, the notation $[\alpha]_q$ (respectively, $[\alpha]_t$) to denote the operation of reducing the coefficients of a∈R modulo q (respectively, t) into the set $\{\lceil -q/2 \rceil, \ldots, \lfloor (q-1)/2 \rfloor\}$ (respectively, $\{\lceil -t/2 \rceil, \ldots, \lfloor (t-1)/2 \rfloor\}$).

In one particular implementation, the computation module 134 can add two ciphertexts $c_1$ and $c_2$, and can output the ciphertext $$c_{add}:=[c_1+c_2]_q \qquad (5)$$

In one particular implementation, the computation module 134 can multiply two ciphertexts, and can output $$c_{mult}:=\left[\left\lfloor \frac{t}{q}(c_1 \cdot c_2) \right\rceil\right]_q \qquad (6)$$

In one particular implementation, the computation module 134 can compute a dot product of a vector of encrypted numbers with a vector of unencrypted coefficients. Such a "plain multiplication" avoids key switching or relinearization, which improves the speed of the processing described herein. This plain multiplication can be described below as $$c_{multplain}:=[p \cdot c]_q \qquad (7)$$

The environment 100 also includes one or more users 138 to employ the computing device 102. The one or more users 138 can interact with the computing device 102 to perform a variety of operations. In some instances, the genomic data module 108 can include genomic data relating to the one or more users 138.

The example processes (e.g., in FIGS. 2-5) are illustrated as logical flow graphs, each operation of which represents a sequence of operations that can be implemented in hardware, software, or a combination thereof. In the context of software, the operations represent computer-executable instructions stored on one or more computer-readable storage media that, when executed by one or more processors, configure a device to perform the recited operations. Generally, computer-executable instructions include routines, programs, objects, components, data structures, and the like that perform particular functions. The order in which the operations are described is not intended to be construed as a limitation, and any number of the described operations can be combined in any order and/or in parallel to implement the process. Further, any of the individual operations can be omitted.

Figure 2:
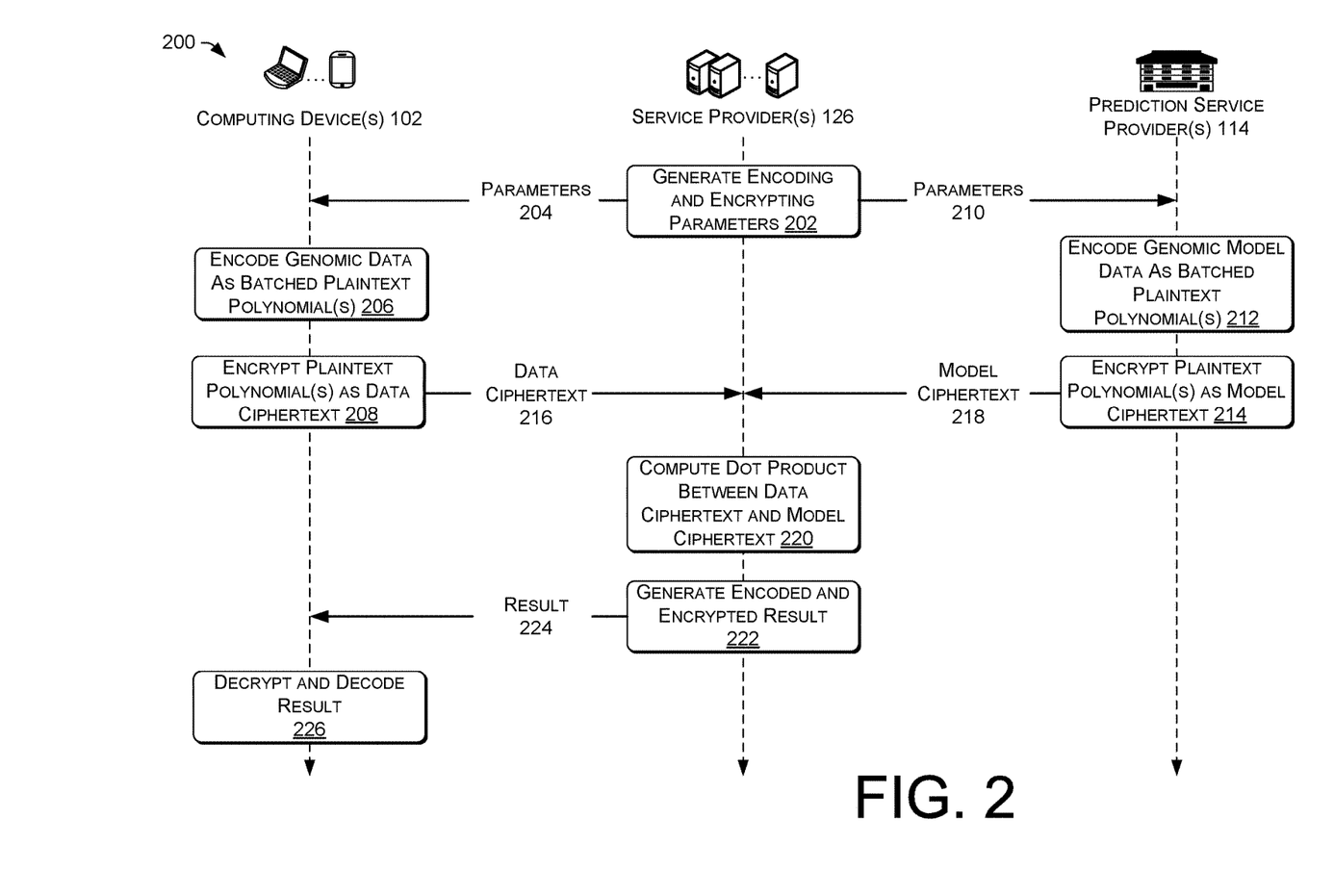
FIG. 2 illustrates an example process for managing secure computations on encrypted data.

FIG. 2 illustrates an example process 200 for managing secure computations on encrypted data, according to one example implementation. By way of example, the process 200 can be performed by and between the computing device(s) 102, the prediction service provider(s) 114, and the service provider(s) 126.

At 202, the service provider 114 can generate encoding and/or encrypting parameters using the parameter selection module 132, for example, of FIG. 1. In some embodiments, the service provider 126 generates the encoding and encrypting parameters in response to a request from the computing device 102 and/or the prediction service provider 114. By way of example, the encoding and encrypting parameters can include, but are not limited to, parameters (n, q, t, $x_{key}$, $x_{err}$). Further details of generating the encoding and encrypting parameters are provided below in connection with FIG. 4.

At 204, the encoding and encrypting parameters can be transmitted to the computing device 102. In some embodiments, the parameters 204 can be encrypted using a public key associated with the computing device 102, to further ensure the security of the data processing.

The computing device 102 can receive the parameters 204, and at 206 can use the encoding parameters to encode genomic data as a batched plaintext polynomial. Further details of encoding data as a plaintext polynomial are discussed in connection with FIGS. 3 and 5, for example.

At 208, the data encoded in operation 206 is encrypted as a ciphertext, based at least in part on the parameters generated by the service provider 126. Because the data is encoded and encrypted by the computing device 102, the security and confidentiality of the data is preserved. In some embodiments, the operation 208 can include generating a public key for encrypting the encoded data, and a private key for decrypting the encrypted data. As can be understood in the context of this disclosure, the public and private keys can be generated at least in part based on the encoding and encrypting parameters generated by the service provider 126 in operation 202.

At 210, the encoding and encrypting parameters generated by the service provider 126 in the operation 202 can be transmitted to the prediction service provider 114. In some embodiments, the parameters 210 can be encrypted using a public key associated with the prediction service provider 114, to further ensure the security of the data processing. In some instances, the parameters 204 can correspond to the parameters 210.

The prediction service provider 114 can receive the parameters 210, and at 212 can use the encoding parameters to encode genomic model data as a batched plaintext polynomial. Further details of encoding data as a plaintext polynomial are discussed in connection with FIGS. 3 and 5, for example.

At 214, the data encoded in operation 212 is encrypted as a ciphertext, based at least in part on the parameters generated by the service provider 126. Because the data is encoded and encrypted by the prediction service provider 114, the security and confidentiality of the data is preserved. In some embodiments, the operation 214 can include generating a public key for encrypting the encoded data, and a private key for decrypting the encrypted data. As can be understood in the context of this disclosure, the public and private keys can be generated at least in part based on the encoding and encrypting parameters generated by the service provider 126 in operation 202. In some instances, the operation 214 can be omitted, and plaintext polynomials can be transmitted to the service provider 126, for example.

At 216, the data ciphertext is transmitted to the service provider 126, and at 218, the model ciphertext is transmitted to the service provider 126. In some instances, the service provider 126 and the prediction service provider 114 may be comprised by a same entity, in which case, the transmission operations between the service provider 126 and the prediction service provider 114 (e.g., operations 210 and 218) can be avoided. After the data ciphertext and the model ciphertext (or the data ciphertext and the model plaintext) is received by the service provider 126, at operation 220, operations can compute the dot product between the data ciphertext and the model ciphertext. Further, because of the process of encoding and encrypting the data, the computations can be performed on the data without decoding or decrypting the data. That is to say, homomorphic operations applied to the encoded and encrypted data can correspond to operations performed on the underlying data, without revealing any information about the contents of the data to the service provider 126. In some embodiments, computations can include addition, subtraction, and/or multiplication.

At 222, an encoded and encrypted result is generated by the service provider 126. As discussed above, a result can be generated without decoding or decrypting the data, which therefore ensures the confidentiality of the data and the result of the operations. For example, if a genomic prediction algorithm performs operations on encoded and encrypted data, the service provider 126 learns nothing about the prediction, other than the fact that operations were performed, which can correspond to a prediction.

In some instances, if homomorphic operations are performed between the data ciphertext and the model ciphertext, the operations will result in an encoded and encrypted result. In some instances, if homomorphic operations are performed between the data ciphertext and a model plaintext, the operations will result in an encoded and encrypted result. In some instances, the operations between a ciphertext and a plaintext improve the processing and memory requirements of the operations, thereby improving a functioning of a computer.

At 224, an encoded and encrypted result is returned to the computing device 102, after which, in operation 226, the computing device 102 can use an associated secret key to decrypt and decode the result to obtain a plaintext result. In some embodiments, the secret key (and the public key, discussed above) can be based at least in part on the encoding and/or encrypting parameters received from the service provider 126, resulting in optimized homomorphic encryption. As may be understood in the context of this disclosure, a plurality of users may encrypt data using the public key, and contribute the data to a computation performed on the service provider 126, but only one user may have the secret key to decrypt any result from the service provider 126. In this manner, optimized computations can be performed remotely without revealing any information about a user's data. In some instances, some or all of the result 224 may be provided to the prediction service provider 114. In some instances, an indication that a result has been obtained using a genomic prediction model can be provided to the prediction service provider 114.

Figure 3:
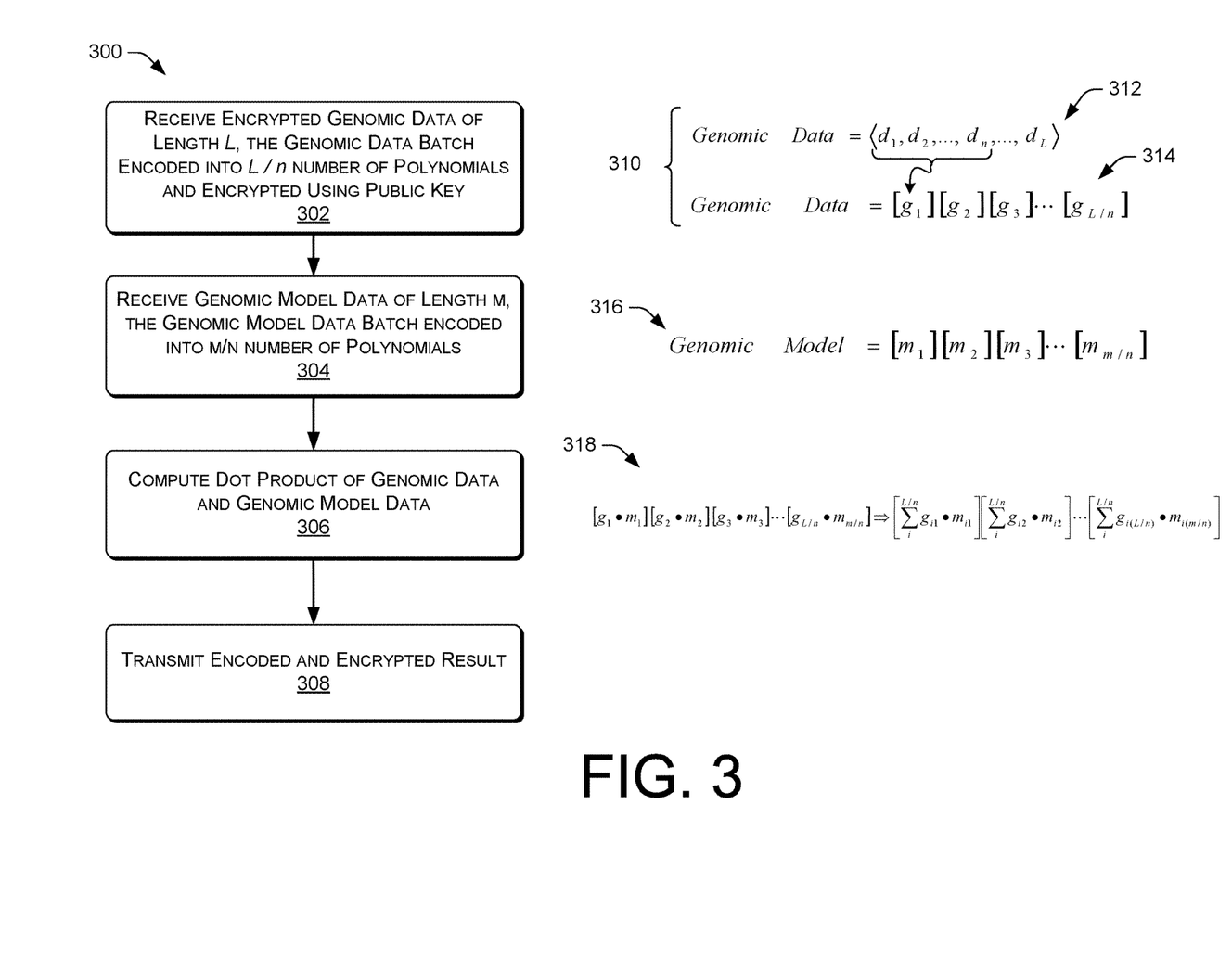
FIG. 3 illustrates an example process for batch encoding genomic data and genomic model data and computing a prediction result.

FIG. 3 illustrates an example process 300 for batch encoding genomic data and genomic model data and computing a prediction result. In one embodiment, the process 300 can be performed by the computation module 134 in the service provider 126 in FIG. 1. In some embodiments, aspects may be performed in the encoding/encrypting modules 110 and 122 in the computing device 102 and/or the prediction service provider 114 of FIG. 1, respectively. However, processes can be performed in other environments and by other devices as well.

In general, the process 300 includes receiving encrypted genomic data in operation 302, which is batch encoded into a plurality of polynomials in a message space of a homomorphic encryption scheme. Similarly, the process include receiving encrypted genomic model data in operation 304, which is batch encoded into a plurality of polynomials in a message space of a homomorphic encryption scheme. Both of the genomic data and the genomic model data can be encrypted at the computing device 102 and the predictive service provide 114, respectively, or at least one of the genomic data or the genomic model data may be encrypted. At 306, a dot product of the genomic data and the genomic model data is computed by the computation module 134 without decrypting or decoding the data, and an encrypted and/or encoded result is transmitted at 308 to either the computing device 102, the predictive service provider 114, or both.

One advantage of the process 300 is by using the batch encoding techniques described herein, an amount of data can be reduced, thereby improving processing operations, reducing an amount of memory required for calculations, and/or reducing an amount of data to be transferred over a network, thereby reducing network congestion. Further, the encoding and/or encrypting parameters can be determined to avoid computationally expensive "bootstrapping" processes to remove noise in the polynomials as operations are performed. Thus, process 300 improves the functioning of the computer by reducing processing and memory requirements while encoding, encrypting, performing computations, and while decrypting and/or decoding an encoded result.

At 302, the operation can include receiving encrypted genomic data of length L, the genomic data having been batch encoded into L/n number of polynomials and encrypted using a public key. An example 310 illustrates the process of batch encoding, as discussed herein.

The example 310 includes a genomic data vector 312 including data of length L. For example, the genomic data vector 312 includes data elements $d_1, d_2, \ldots, d_n, \ldots, d_L$, where L is greater than n. In some instances, the parameter n refers to the maximum number of terms in the polynomials in the homomorphic encryption scheme, as discussed above. In some instances, the length L is determined by an amount of genes and/or traits associated with a particular genomic prediction.

In some instances, additional zeros or other padding data can be appended to genomic data vector such that the length of the genomic data vector is evenly divisible by the parameter n. That is, L modulo n=0. By way of example, and without limitation, for a genomic data vector containing 205113 elements, 1735 zeros can be appended to the genomic data vector such that an adjusted genomic data vector containing 206848 elements can be equally divided into polynomials of length n=2048.

The example 310 also includes genomic data 314 with L/n number of polynomials and n number of slots in each polynomial. Further, n number of data elements from the genomic data vector 312 can be encoded into the n number of slots. For example, elements $d_1, d_2, \ldots, d_n$ are encoded as a batch into a first polynomial $g_1$. In some instances, the polynomial $g_1$ can correspond to a polynomial of length n.

Batching is a technique to pack n plaintext integers modulo t into one plaintext polynomial in $R_t$. As n can be on the order of thousands of elements, it can be understood that batching can result in a significant improvement in the computational cost of encrypting the data. As the size of ciphertext polynomials can be large, unbatched polynomials can cause a problem when the number of the polynomials is in the hundreds of thousands or millions. Instead, with batching the total memory cost is roughly to be divided by n. Furthermore, in some instances, batching allows SIMD (Single Instruction Multiple Data) operations performed on the batched data, which further improves the functioning of the computer by performing n homomorphic additions or multiplications of integers modulo t at the cost of one (unbatched) operation.

The batching process is explained herein. If t is a prime number such that $t \equiv 1 \pmod{2n}$, then the plaintext space $R_t$ is isomorphic as a ring to n-fold product $\mathbb{Z}_t \times \ldots \times \mathbb{Z}_t$. Further, each n-tuple of numbers modulo t can be composed into a unique polynomial in a way that respects both addition and multiplication. In other words, adding together two such composed polynomials results in a polynomial where the i-th slot contains the sum modulo t of the values in the i-th slots of the two polynomials. The same holds for multiplication.

Further, if $t \equiv 1 \pmod{2n}$, then there is an element $\zeta \in \mathbb{Z}_t$ such that all powers of $\zeta$ up to $\zeta^{2n-1}$ are distinct and $$X^n + 1 = (X-\zeta)(X-\zeta^3) \ldots (X-\zeta^{2n-1}) \pmod{t} \tag{8}$$

Denoting $\alpha_i := \zeta^{2i-1}$, so that $X^n+1 = \Pi(x-\alpha_i) \pmod{t}$. Further, for each $i=1, \ldots, n$, polynomials can be defined as $$\tilde{f}_i(X) := \frac{X^n + 1}{X - \alpha_i} \in R_t \tag{9}$$

Thus, a property of $\tilde{f}_i(X)$ is that that $\tilde{f}_i(\alpha_j)=0$ if $j \neq i$. Next, for each $i=1, \ldots, n$, let $f_i(X):=\tilde{f}_i(X)/\tilde{f}_i(\alpha_i) \in R_t$. In some instances, the integer $\tilde{f}_i(\alpha_i)$ can automatically be invertible modulo t, as t is taken to be a prime. In some instances, the set of polynomials $f_i(X)$ can be referred to as the CRT (Chinese Remainder Theorem) basis of $R_t$. Further, the polynomials $f_i(X)$ have a nice property such that $f_j(\alpha_i)=1$ if $j=i$ and 0 if $j \neq i$. The correspondence $R_t \cong \mathbb{Z}_t \times \ldots \times \mathbb{Z}_t$ maps the n-tuple $\overline{\lambda}:=(\lambda_1, \ldots, \lambda_n)$ of integers modulo t to the polynomial $$\text{Compose}(\overline{\lambda}) := \Sigma_{i=1}^n \lambda_i f_i(X) \tag{10}$$

In some instances, the tuple $\overline{\lambda}$ can be recovered by evaluating the composed polynomial at the various $\alpha_i$, as $\text{Compose}(\overline{\lambda})(\alpha_i)=\lambda_i$ due to the properties of the $f_i(X)$. In other words, given a composed polynomial $h \in R_t$, a decompose operation can be defined as $$\text{Decompose}(h) := (h(\alpha_1), \ldots, h(\alpha_n)) \in (\mathbb{Z}_t)^{\times n} \tag{11}$$

So that $\text{Decompose}(\text{Compose}(\overline{\lambda}))=\overline{\lambda}$.

Further, the compose operation behaves as follows $$\text{Compose}(\overline{\lambda}_1) + \text{Compose}(\overline{\lambda}_2) = \text{Compose}(\overline{\lambda}_1 + \overline{\lambda}_2) \tag{12}$$

If $\overline{\lambda}_1 \odot \overline{\lambda}_2$ denote the element-wise product of the two vectors, then also $$\text{Compose}(\overline{\lambda}_1) \cdot \text{Compose}(\overline{\lambda}_2) = \text{Compose}(\overline{\lambda}_1 \odot \overline{\lambda}_2) \tag{13}$$

where the product on the left-hand side is computed in $R_t$. This can be verified by an explicit computation using the $f_i(X) \cdot f_j(X) = 0 \in R_t$ if $j \neq i$ and $f_i(X)^2 = f_i(X) \in R_t$ for every i, as a non-zero polynomial of degree n−1 can have at most n−1 distinct roots. Both $f_i(X) \cdot f_j(X) = 0 \in R_t$ if $j \neq i$ and $f_i(X)^2 - f_i(X) \in R_t$ for every i are polynomials of degree n−1, but they have n roots, namely all $\alpha_1, \ldots, \alpha_n$. Thus, both polynomials can be zero in $R_t$.

In light of the instant dot product computations between genomic data and genomic model data, an alternate implementation of the batching follows. Consider $$\widetilde{\text{Compose}}(\overline{\lambda}) := \Sigma_{i=1}^n \lambda_i \tilde{f}_i(X) \tag{14}$$

Each of the polynomials $\tilde{f}_i(X)$ can have the form $X^{n-1} + \ldots$, so $$\widetilde{\text{Compose}}(\overline{\lambda}) := (\Sigma_{i=1}^n \lambda_i) X^{n-1} + \ldots \tag{15}$$

which leads to the property that the sum (e.g., the genomic result in the dot product between genomic data and genomic model data) can be read simply by looking at the leading coefficient. Accordingly $$\widetilde{Compose}(\bar{\lambda}_1) + \widetilde{Compose}(\bar{\lambda}_2) = \widetilde{Compose}(\bar{\lambda}_1 + \bar{\lambda}_2) \quad (16)$$

and $$\widetilde{Compose}(\bar{\lambda}_1) \cdot Compose(\bar{\lambda}_2) = \widetilde{Compose}(\lambda_1 \odot \lambda_2) \quad (17)$$

At 304, the operation can include receiving genomic model data of length m, the genomic mode data batch encoded into m/n number of polynomials, as discussed above. An example 316 illustrates the genomic mode encoded into m/n number of polynomials.

At 306, the operation can include computing the dot product of the genomic data and the genomic model data. As discussed above, because of the batch encoding of the genomic data and the genomic model data, the resulting polynomial includes a leading coefficient (e.g., the coefficient of $X^{n-1}$) such that the leading coefficient is the sum of all the slots of the various polynomials, which corresponds to the genomic result. An example 318 illustrates an expansion of the dot product operations described herein.

At 308, the operation can include transmitting the encoded and encrypted result to the computing device 102 and/or to the prediction service provider 114.

Figure 4:
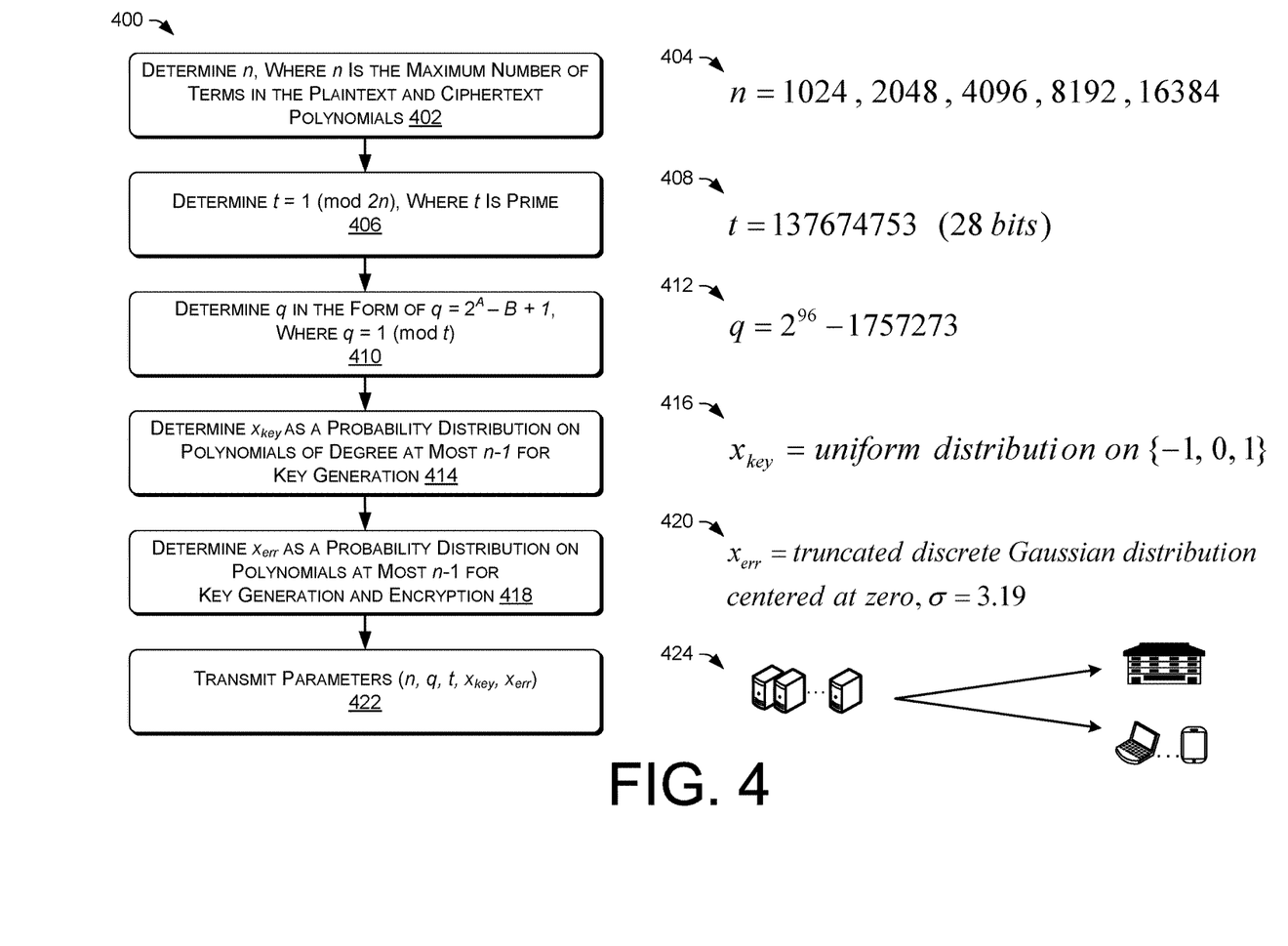
FIG. 4 illustrates an example process for determining encoding and encrypting parameters for secure computations.

FIG. 4 illustrates another example process 400 for determining encoding and encrypting parameters for secure computations. In one embodiment, the process 400 can be performed by the parameter selection module 132 in the service provider 126 in FIG. 1. However, processes can be performed in other environments and by other devices as well.

In general, the process 400 includes determining the encoding/encryption parameters parms:=$(n,q,t,x_{key},x_{err})$. Following the generation of the parameters, the parameters can be transmitted to the computing device 102 and/or the prediction service provider 114 to facilitate the encoding and encrypting of genomic data and/or genomic model data for genomic predictions using homomorphic operations.

One advantage of the process 400 is that optimizing parameters for encoding and encrypting allows for security and confidentiality of data to be maintained while improving the processing requirements and memory requirements of the homomorphic operations. For example, the parameters can be tailored to generate polynomials large enough to guarantee operation in a worst-case scenario or an average-case scenario, without being too large as to become unmanageable. Further, an optimization of parameters allows homomorphic operations to be performed without performing any "bootstrapping" or relinearization processes. Therefore, the process 400 can improve processing abilities for a given application, program, or operation, and can improve the functioning of the computer by improving processing abilities and improving memory requirements when performing homomorphic operations.

At 402, the operation can include determining n, where n is a maximum number of terms n in the plaintext and ciphertext polynomials, as discussed herein. By way of example 404, n can be a power of 2. Representative values of n include, but are not limited to, n=1024, 2048, 4096, 8192, 16384, etc. In some instances, as n increases, a level of security increases. However, an amount of processing increases with n, therefore suggesting a balance between security and processing performance.

At 406, the operation can include determining t=1 (mod 2n), where t is a prime number. By way of example, and without limitation, choosing n=2048, example 408 illustrates t=137674753.

At 410, the operation can include determining q in the form of q=$2^A$–B+1, where q=1 (mod t). By way of example, and without limitation, example 412 illustrates that q=$2^{96}$–1757273.

At 414, the operation can include determining $x_{key}$ as a probability distribution on polynomials of degree at most n–1 for key generation. As illustrated in example 416, and without limitation, the probability distribution can be a uniform distribution on the set {–1, 0, 1}.

At 418, the operation can include determining $x_{err}$ as a probability distribution on polynomials at most n–1 for key generation and encryption. As illustrated in example 420, and without limitation, the probability distribution can be a truncated discrete Gaussian distribution centered at zero, with a standard deviation σ=3.19.

At 422, the operation can include transmitting the parameters (n, q, t, $x_{key}$, $x_{err}$) from the service provider 126 to one or more of the computing devices 102 or the prediction service provider 114, for example, as illustrated in example 424 and in accordance with embodiments of the disclosure.

In some instances, applying the optimized parameters discussed in connection with FIG. 4 to genomic data results in improved performance of the genomic prediction. For example, taking n=2048, t=137674753, q=$2^{96}$–1757273 and applying the parameters to a genomic data vector of 205,113 elements results in 101 encoded and encrypted polynomials, each of the polynomials having 2048 coefficients, with each polynomial stored in two 64-bit words. Thus, in this example, the encrypted data can be stored in 3.16 MB of data, and an encrypted result can have a size of 32 KB. In some instances, coefficient vectors include zeros as most significant bits, leading to further optimization, allowing the encrypted data to be stored in 2.37 MB. In contrast, not using the techniques discussed herein may result in encrypted data on the order of gigabytes, instead of megabytes.

Figure 5:
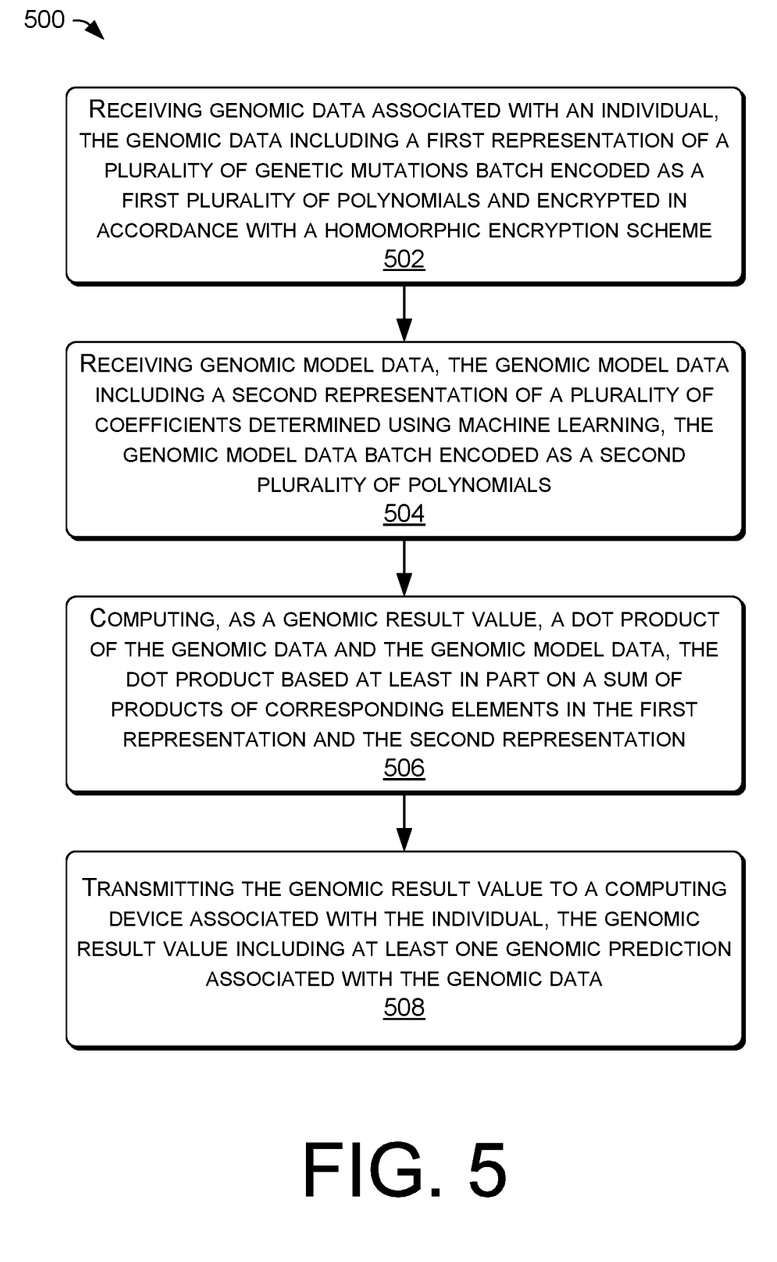
FIG. 5 illustrates an example process for performing a genomic prediction in a secure computing environment.

FIG. 5 illustrates an example process 500 for performing a genomic prediction in a secure computing environment. In one embodiment, the process 500 can be performed by the computation module 134 in the service provider 126 in FIG. 1. In some embodiments, aspects may be performed in the encoding/encrypting modules 110 and 122 in the computing device 102 and/or the prediction service provider 114 of FIG. 1, respectively. However, processes can be performed in other environments and by other devices as well.

At 502, receiving genomic data associated with an individual, the genomic data including a first representation of a plurality of genetic mutations batch encoded as a first plurality of polynomials and encrypted in accordance with a homomorphic encryption scheme.

At 504, the operation can include receiving genomic model data, the genomic model data including a second representation of a plurality of coefficients determined using machine learning, the genomic model data batch encoded as a second plurality of polynomials. In some instances, the genomic model vector can be batch encoded as discussed herein. In some instances, the genomic model vector can be encrypted as a ciphertext or can remain unencrypted as plaintext data.

At 506, the operation can include computing, as a genomic result value, a dot product of the genomic data and the genomic model data, the dot product based at least in part on a sum of products of corresponding elements in the first representation and the second representation.

At 508, the operation can include transmitting the genomic result value to a computing device associated with the individual, the genomic result value including at least one genomic prediction associated with the genomic data.

EXAMPLE CLAUSES

Example A, a system comprising: one or more processors; and memory storing modules that, when executed by the one or more processors, cause the system to perform operations comprising: receiving genomic data associated with an individual, the genomic data including a first representation of a plurality of genetic mutations batch encoded as a first plurality of polynomials and encrypted in accordance with a homomorphic encryption scheme; receiving genomic model data, the genomic model data including a second representation of a plurality of coefficients determined using machine learning, the genomic model data batch encoded as a second plurality of polynomials; computing, as a genomic result value, a dot product of the genomic data and the genomic model data, the dot product based at least in part on a sum of products of corresponding elements in the first representation and the second representation; and transmitting the genomic result value to a computing device associated with the individual, the genomic result value including at least one genomic prediction associated with the genomic data.

Example B, the system of Example A, the operations further comprising: representing the plurality of genetic mutations as a plurality of genomic data vectors of length m, wherein a polynomial of the first plurality of polynomials includes at most n number of terms; and encoding the plurality of genomic data vectors as the first plurality of polynomials, the first plurality of polynomials consisting of m/n polynomials.

Example C, the system of Example A or Example B, wherein a polynomial of the second plurality of polynomials associated with the genomic model data is a plaintext polynomial.

Example D, the system of any one of Example A through Example C, wherein the genomic result value is associated with a third plurality of polynomials, and wherein the computing the genomic result value includes homomorphically adding coefficients associated with the third plurality of polynomials.

Example E, the system of any one of Example A through Example D, wherein the genomic result value is associated with a highest-degree term, and wherein a coefficient associated with the highest-degree term represents an evaluation of the dot product of the genomic data and the genomic model data.

While Example A through Example E are described above with respect to a system, it is understood in the context of this document that the content of Example A through Example E may also be implemented via a device, computer storage media, and/or a method.

Example F, a computer-implemented method comprising: receiving, from a computing device as received genomic data, a first representation of genomic data batch encoded as a first plurality of polynomials and encrypted in accordance with a homomorphic encryption scheme; receiving, from a prediction service provider as received genomic model data, a second representation of coefficients of a genomic model batch encoded as a second plurality of polynomials; computing, as a genomic result value, a dot product of the received genomic data and the received genomic model data; and transmitting the genomic result value to the computing device, the genomic result value including at least one genomic prediction associated with the genomic data.

Example G, the computer-implemented method of Example F, wherein polynomials of the first plurality of polynomials are represented in the received genomic data as homomorphically encrypted genomic data vectors.

Example H, the computer-implemented method of Example F or Example G, further comprising: generating, at a service provider, encryption parameters associated with the homomorphic encryption scheme; and transmitting the encryption parameters to at least the computing device associated with the genomic data, wherein the received genomic data is batch encoded as the first plurality of polynomials based at least in part on the encryption parameters.

Example I, the computer-implemented method of Example H, wherein the encryption parameters include at least a plaintext modulus t and at least a size of a polynomial n, and wherein the generating the encoding parameters includes determining the plaintext modulus t such that the plaintext modulus t modulo a value twice the size of the polynomial n is equal to 1.

Example J, the computer-implemented method of Example I, wherein the encryption parameters further includes at least a coefficient modulus q, and wherein the generating the encryption parameters further includes determining the coefficient modulus q such that the coefficient modulus q modulo the plaintext modulus t is equal to 1.

Example K, the computer-implemented method of any one of Example F through Example J, wherein the computing the dot product includes computing the dot product between a genomic data vector associated with the received genomic data and a genomic model vector associated with the received genomic model data.

Example L, the computer-implemented method of Example K, wherein the computing the dot product between the genomic data vector and the genomic model vector provides the genomic result value as an encrypted value.

Example M, the computer-implemented method of any one of Example F through Example L, wherein the computing the dot product includes at least one homomorphic multiplication operation and at least one homomorphic addition operation.

Example N the computer-implemented method of any one of Example F through Example M, wherein the genomic result value is associated with a third plurality of polynomials, and wherein the computing the genomic result value includes homomorphically adding coefficients associated with the third plurality of polynomials.

Example O, the computer-implemented method of Example N, wherein the genomic result value is associated with a highest-degree term, and wherein a coefficient associated with the highest-degree term represents the dot product of the genomic data and the genomic model data.

While Example F through Example O are described above with respect to a method, it is understood in the context of this document that the content of Example F through Example O may also be implemented via a device, system, and/or computer storage media.

Example P, a system comprising: one or more processors; and memory storing modules that, when executed by the one or more processors, cause the system to perform operations comprising: receiving, as received genomic data, a first representation of genomic data batch encoded as a first plurality of polynomials and encrypted in accordance with a homomorphic encryption scheme; receiving, as received genomic model data, a second representation of coefficients of a genomic model batch encoded as a second plurality of polynomials; computing, as a genomic result value, a dot product of the received genomic data and the received genomic model data; and transmitting the genomic result value to a computing device, the genomic result value including at least one genomic prediction associated with the genomic data.

Example Q, the system of Example P, the operations further comprising: representing the genomic data as a plurality of genomic data vectors of length m, wherein a polynomial of the first plurality of polynomials includes at most n number of terms, and encoding the plurality of genomic data vectors as the first plurality of polynomials, the first plurality of polynomials consisting of m/n polynomials.

Example R, the system of Example P or Example Q, the operations further comprising: generating encryption parameters associated with the homomorphic encryption scheme; and transmitting the encryption parameters to at least the computing device associated with the genomic data.

Example S, the system of Example R, wherein the received genomic data is batch encoded as the first plurality of polynomials based at least in part on the encryption parameters.

Example T, the system of any one of Example P through Example S, wherein the computing the dot product includes at least one homomorphic multiplication operation and at least one homomorphic addition operation.

While Example P through Example T are described above with respect to a system, it is understood in the context of this document that the content of Example P through Example T may also be implemented via a device, computer storage media, and/or a method.

CONCLUSION

Although the present disclosure can use language that is specific to structural features and/or methodological operations, the disclosure is not limited to the specific features or operations described herein. Rather, the specific features and operations are disclosed as illustrative forms of implementing the disclosure.

What is claimed is:

1. A system comprising:
   one or more processors; and
   memory storing modules that, when executed by the one or more processors, cause the system to perform operations comprising:
   receiving genomic data associated with an individual, the genomic data including a first representation of a plurality of genetic mutations batch encoded as a first plurality of polynomials and encrypted in accordance with a homomorphic encryption scheme;
   receiving genomic model data, the genomic model data including a second representation of a plurality of coefficients determined using machine learning, the genomic model data batch encoded as a second plurality of polynomials;
   computing, as a genomic result value, a dot product of the genomic data and the genomic model data, the dot product based at least in part on a sum of products of corresponding elements in the first representation and the second representation; and
   transmitting the genomic result value to a computing device associated with the individual, the genomic result value including at least one genomic prediction associated with the genomic data.

2. The system of claim 1, the operations further comprising:
   representing the plurality of genetic mutations as a plurality of genomic data vectors of length m, wherein a polynomial of the first plurality of polynomials includes at most n number of terms; and
   encoding the plurality of genomic data vectors as the first plurality of polynomials, the first plurality of polynomials consisting of m/n polynomials.

3. The system of claim 1, wherein a polynomial of the second plurality of polynomials associated with the genomic model data is a plaintext polynomial.

4. The system of claim 1, wherein the genomic result value is associated with a third plurality of polynomials, and wherein the computing the genomic result value includes homomorphically adding coefficients associated with the third plurality of polynomials.

5. The system of claim 4, wherein the genomic result value is associated with a highest-degree term, and wherein a coefficient associated with the highest-degree term represents an evaluation of the dot product of the genomic data and the genomic model data.

6. A computer-implemented method comprising:
   receiving, from a computing device as received genomic data, a first representation of genomic data batch encoded as a first plurality of polynomials and encrypted in accordance with a homomorphic encryption scheme;
   receiving, from a prediction service provider as received genomic model data, a second representation of coefficients of a genomic model batch encoded as a second plurality of polynomials;
   computing, as a genomic result value, a dot product of the received genomic data and the received genomic model data; and
   transmitting the genomic result value to the computing device, the genomic result value including at least one genomic prediction associated with the genomic data.

7. The computer-implemented method of claim 6, wherein polynomials of the first plurality of polynomials are represented in the received genomic data as homomorphically encrypted genomic data vectors.

8. The computer-implemented method of claim 6, further comprising:
   generating, at a service provider, encryption parameters associated with the homomorphic encryption scheme; and
   transmitting the encryption parameters to at least the computing device associated with the genomic data,
   wherein the received genomic data is batch encoded as the first plurality of polynomials based at least in part on the encryption parameters.

9. The computer-implemented method of claim 8, wherein the encryption parameters include at least a plaintext modulus t and at least a size of a polynomial n, and wherein the generating the encoding parameters includes determining the plaintext modulus t such that the plaintext modulus t modulo a value twice the size of the polynomial n is equal to 1.

10. The computer-implemented method of claim 9, wherein the encryption parameters further includes at least a coefficient modulus q, and wherein the generating the encryption parameters further includes determining the coefficient modulus q such that the coefficient modulus q modulo the plaintext modulus t is equal to 1.

11. The computer-implemented method of claim 6, wherein the computing the dot product includes computing the dot product between a genomic data vector associated with the received genomic data and a genomic model vector associated with the received genomic model data.

12. The computer-implemented method of claim 11, wherein the computing the dot product between the genomic data vector and the genomic model vector provides the genomic result value as an encrypted value.

13. The computer-implemented method of claim 6, wherein the computing the dot product includes at least one homomorphic multiplication operation and at least one homomorphic addition operation.

14. The computer-implemented method of claim 6, wherein the genomic result value is associated with a third plurality of polynomials, and wherein the computing the genomic result value includes homomorphically adding coefficients associated with the third plurality of polynomials.

15. The computer-implemented method of claim 14, wherein the genomic result value is associated with a highest-degree term, and wherein a coefficient associated with the highest-degree term represents the dot product of the genomic data and the genomic model data.

16. A system comprising:
one or more processors; and
memory storing modules that, when executed by the one or more processors, cause the system to perform operations comprising:
receiving, as received genomic data, a first representation of genomic data batch encoded as a first plurality of polynomials and encrypted in accordance with a homomorphic encryption scheme;
receiving, as received genomic model data, a second representation of coefficients of a genomic model batch encoded as a second plurality of polynomials;
computing, as a genomic result value, a dot product of the received genomic data and the received genomic model data; and
transmitting the genomic result value to a computing device, the genomic result value including at least one genomic prediction associated with the genomic data.

17. The system as recited in claim 16, the operations further comprising:
representing the genomic data as a plurality of genomic data vectors of length m, wherein a polynomial of the first plurality of polynomials includes at most n number of terms, and
encoding the plurality of genomic data vectors as the first plurality of polynomials, the first plurality of polynomials consisting of m/n polynomials.

18. The system as recited in claim 16, the operations further comprising:
generating encryption parameters associated with the homomorphic encryption scheme; and
transmitting the encryption parameters to at least the computing device associated with the genomic data.

19. The system as recited in claim 18, wherein the received genomic data is batch encoded as the first plurality of polynomials based at least in part on the encryption parameters.

20. The system as recited in claim 16, wherein the computing the dot product includes at least one homomorphic multiplication operation and at least one homomorphic addition operation.

\* \* \* \* \*